United States Patent [19]

Cislo

[11] 4,122,035

[45] Oct. 24, 1978

[54] PROCESS FOR RECLAIMING SYNTHETIC MAGNESIUM SILICATE OR ALUMINUM SILICATE ADSORBENTS EMPLOYED IN THE PURIFICATION OF POLYETHER POLYOLS

[75] Inventor: Carl Casimer Cislo, Wyandotte, Mich.

[73] Assignee: BASF Wyandotte Corporation, Wyandotte, Mich.

[21] Appl. No.: 751,736

[22] Filed: Dec. 17, 1976

[51] Int. Cl.$^2$ .................... B01J 21/20; C07H 15/08; C07C 43/00
[52] U.S. Cl. .................... 252/414; 260/568; 260/573; 260/584 C; 260/611 B; 260/613 B; 260/615 B; 536/1; 536/4; 536/120; 544/401; 544/374
[58] Field of Search ............... 252/414, 420, 413, 415; 210/30, 32, 38; 260/615 B; 536/4, 120

[56] References Cited

U.S. PATENT DOCUMENTS

| | | | |
|---|---|---|---|
| 2,913,501 | 11/1959 | Cahill, Jr. ................ | 260/643 G |
| 2,992,180 | 7/1961 | Schatz et al. ............ | 252/414 |
| 3,326,875 | 6/1967 | Moore ..................... | 260/615 B |
| 3,356,738 | 12/1967 | Hauser et al. ............ | 260/615 B |
| 4,029,879 | 6/1977 | Muzzio .................... | 260/615 B |

FOREIGN PATENT DOCUMENTS

| | | | |
|---|---|---|---|
| 45-32,432 | 10/1970 | Japan ..................... | 260/615 B |
| 197,158 | 5/1967 | U.S.S.R. ................. | 260/615 B |

*Primary Examiner*—P. E. Konopka
*Attorney, Agent, or Firm*—Robert J. Henry; Bernhard R. Swick; Robert E. Dunn

[57] ABSTRACT

A process for recovering a catalyst adsorbent from a polyol-adsorbent residue by treatment of the polyol-adsorbent residue with organic solvents. This adsorbent can then be recycled for use in the further removal of alkaline catalysts from polyether polyols.

5 Claims, No Drawings

PROCESS FOR RECLAIMING SYNTHETIC MAGNESIUM SILICATE OR ALUMINUM SILICATE ADSORBENTS EMPLOYED IN THE PURIFICATION OF POLYETHER POLYOLS

BACKGROUND OF THE INVENTION

1. Field of the Invention

Polyoxyalkylene ether polyols hereinafter for convenience called polyols are commonly used in the production of urethane polymers. The said polyols are reacted with polyisocyanate in the presence of added catalyst and other materials to produce the urethane polymers which may be in the form of rubber-like elastomers, foams of flexible or rigid character, and the like. In order that urethane polymers of desired properties and characteristics are produced, it is importat that the polyols to be reacted with the polyisocyanate are essentially free of impurities which may function as undesirable catalysts or otherwise react undesirably in the urethane polymer reaction. Polyols as commercially prepared in the crude form contain alkali metal hydroxides or other metal salts. The normal concentration of catalysts range from 1000 to 3000 parts per million expressed as potassium. It is generally desirable to reduce this catalyst concentration to a level of about 10 parts per million or less.

2. Prior Art

There are a number of commercial practices employed for the removal of the catalyst impurities from polyols. Among these are included the neutralization of the catalysts by acids, forming insoluble salts and the removal of these salts by filtration. Other commercial practices involve centrifugation of a mixture of polyol, water and solvent. Ion exchange procedures may also be employed for the removal of catalysts. One commercial procedure for the removal of the catalyst without prior neutralization is treatment with a synthetic type adsorbent material such as magnesium silicate followed by the filtration of the resulting mixture. The process employing such a technique results in an adsorbent residue which contains an amount of polyol which may be equal to that of the adsorbent. The disposal of this spent adsorbent residue presents both ecological and safety problems. Generally speaking, the polyols themselves are not biodegradable and disposal of the adsorbent residue in a landfill is not desirable. The adsorbent wet with polyol, if allowed to remain exposed to the atmosphere, becomes pyrophoric and creates a safety hazard. Thus it is desirable to eliminate the necessity for the disposal of this spent adsorbent polyol residue. While the technical literature does teach the use of adsorbent for catalyst removal there is no teaching whatsoever that the adsorbent can be recycled and further use made thereof.

SUMMARY OF THE INVENTION

It has been discovered that a catalyst adsorbent may be recovered from a polyol-adsorbent residue by treatment with any solvent which is inert with respect to the polyol, catalyst or adsorbent.

DESCRIPTION OF THE PREFERRED EMBODIMENT

The process for recovering the catalyst adsorbent from a polyol-adsorbent residue involves reclamation of the adsorbent by washing the polyol-adsorbent residue with an organic solvent which is compatible with the polyol and subsequently reusing the recovered adsorbent for purification of additional crude polyol. We have found that the most desirable procedure for the removal of the polyols from the polyol-adsorbent residue is by repetitive additions of solvent to the residue with adequate agitation and filtration after each agitation. Thus in the preferred embodiment the amount of solvent which is employed is in the order of about 5 parts of solvent per 1 part of polyol which has been adsorbed onto the adsorbent. It has also been found that the most efficient procedure is to agitate or slurry the polyol-adsorbent residue with the solvent since attempts to wash out the polyol by percolation of solvent through it were not very effective. The temperature at which the washing may take place can occur from about room temperature of about 25° centigrade to the boiling point of the solvent. However in those cases if a sufficiently high boiling solvent be employed it is best not to exceed the temperature of 130° centigrade since degradation of the polyol may occur. The time of agitation will depend on how well the polyol-adsorbent residue is dispersed in the solvent and the amount of solvent employed. After the polyol-adsorbent residue has been sufficiently washed to remove the polyols, the recovered adsorbent can then be either dried by suitable means at temperatures of 90°-100° centigrade or it can even be air dried depending on the particular solvent employed. It is desirable to remove the solvent from the adsorbent before the adsorbent is reused. Upon sufficient drying and the removal of the solvent the adsorbent can then be employed in treating another quantity of crude polyol containing alkaline catalysts in manners which are well known to those skilled in the art.

In general, the impurities present in the polyol which must be removed are the catalysts used in the preparation of the polyol. These catalysts are generally alkali metal hydroxide or alkali metal alkoxides such as sodium hydroxide, potassium hydroxide, sodium alkoxide, potassium alkoxide, etc. Other catalysts which may be employed in the preparation of such polyols and which may be removed by the improved instant process include the hydroxides and alkoxides of lithium, rubidium and cesium.

The polyols purified in accordance with the present invention include those polyols prepared by condensing alkylene oxides such as ethylene oxide, propylene oxide, butylene oxide, and mixtures thereof with active hydrogen compounds such as ethylene glycol, propylene glycol, water, diethylene glycol, dipropylene glycol, trimethylene glycol, 1,2-butanediol 1,3-butanediol, 1,4-butanediol, hexanetriol, glycerol, trimethylolpropane, trimethylolethane, hydroquinone, pentaerythritol, α-methylglucoside, sorbitol, sucrose, ethylene diamine, diethylene triamine, toluene diamine, aniline, methylene dianiline, piperazine, triisopropanolamine, and bisphenol A wherein these polyols have a molecular weight range from about 300 to about 26,000.

Included are those polyols which are characterized as being essentially hydroxyl terminated polyether polyols which have the general formula:

$$H(OR)_nOH$$

wherein R is an alkylene radical and $n$ is an integer which in a preferred embodiment is sufficiently large that the compound, as a whole has a molecular weight from about 300 to about 26,000. These would include polyoxyethylene glycol, polyoxypropylene glycol, and polyoxybutylene glycol. Other typical polyols include block copolymers, e.g., combinations of polyoxypropylene and polyoxyethylene glycols, more specifically those having the general formula:

$$HO(C_2H_4O)_n(C_3H_6O)_m(C_2H_4O)_nH$$

wherein $n$ and $m$ are together sufficient for attainment of the desired minimum molecular weight, that is, about 300. Also included are block copolymers of poly-1,2-oxybutylene and polyoxyethylene glycols and poly-1,4-oxybutylene and polyoxypropylene glycols and random copolymer glycols prepared from addition of blends of two or more alkylene oxides as well as glycols as described above capped with the ethylene oxide units. The polyols purified in accordance with this invention can contain arylene or cycloalkylene radicals together with the alkylene radicals. In such products the cyclic groups inserted in a polyether chain are preferably phenylene, naphthalene, or cyclohexylene radicals or those radicals containing alkyl or alkylene substituents as in the tolylene, phenylethylene or xylylene radicals.

The adsorbents which may be employed in the practice of this invention are those which will remove the alkaline catalysts. These are the synthetic magnesium and aluminum silicate adsorbents. The synthetic adsorbents may be prepared by the reaction of a magnesium salt or aluminum salt such as magnesium or aluminum sulfate with sodium silicate. The resulting products can have particle sizes ranging from 5 to 500 microns with an average particle size of about 100–200 microns. Such magnesium silicate adsorbents are sold under the trademarks of "BRITE SORB" by Philadelphia Quartz Corporation, and "MAGNESOL" by Reagent Chemicals. The amount of adsorbent which can be employed depends on the concentration of catalyst present in the polyol. Thus, amounts ranging from about 0.1 percent to about 5 percent by weight based on the weight of the polyol may be employed. Preferably, however, the concentration of adsorbent ranges from about 1.0 percent to about 4.0 percent based on the weight of polyol. From an economical point of view it is preferable to use as little as possible of the adsorbent.

Any solvent or solvent mixture which is relatively inert with respect to the polyol, the catalyst or the adsorbent and which is miscible with the polyol may be employed. Included are the aliphatic, alicyclic, aromatic hydrocarbons, dialkyl ketones, alkanols, dialkyl ethers, cyclic ethers, hydroxyalkyl ethers and halogenated hydrocarbons. Representative of the above are the butanes, pentanes, hexanes, heptanes, octanes, nonanes, decanes, dodecanes, cyclohexane, methylcyclohexane, cyclopentane, benzene, toluene, xylene, mesitylene, acetone, methylethylketone, methyl isobutylketone, methanol, ethanol, propanol, isopropanol, butanol, pentanol, methylether, ethylether, isopropylether, chloroform, carbon tetrachloride, methyl chloroform, perchloroethylene, dichlorodifluoromethane, 1,1,2-trichloro-1,2,2-trifluoroethane, and trichlorofluoromethane, furan, dioxane, and the mono and dimethyl ethers of ethylene glycol and diethylene glycol. The polar solvents are preferred.

EXAMPLE 1

Into a 2-liter, 3-necked round bottom flask was charged 1000 grams of polyol adsorbent residue composed of approximately 50 percent magnesium silicate adsorbent and 50 percent polyol. The filter cake was slurried 3 times with 500 mls of hexane for one hour each, then filtered each time. This filter cake was then slurried with 1000 mls of methanol for 1 hour and filtered. A 100 gram portion of the filter cake was then charged to a flask and slurried 5 times with 500 ml portions of distilled water. The washed adsorbent was then dried in an oven at 90°–100° C for 16 hours. Crude polyol, a glycerine-propylene oxide-ethylene oxide adduct having a molecular weight of about 6500 and containing about 15 percent oxyethylene and having an alkalinity of about 3000 ppm expressed as K was treated with the washed adsorbent employing 500 grams of polyol, 20 grams of adsorbent and 5 grams of water. The mixture was charged into a flask, stirred at 90°–95° C for 1 hour and then filtered. The stripped polyol resulting from this filtration was found to have an alkalinity of less than 2 ppm expressed as K.

EXAMPLE 2

The final polyol adsorbent residue from Example 1 was slurried 3 times with 50 ml portions of hexane for 1 hour and filtered each time. This adsorbent was then slurried 3 times with 50 ml portions of distilled water for 1 hour and filtered each time. The adsorbent was then dried in an oven at 95° C for 16 hours. Another portion of the crude glycerine based polyol of Example 1 was treated in a manner similar to that employed in Example 1. The polyol resulting from this treatment had an alkalinity of less than 2 ppm expressed as K. The resulting polyol adsorbent residue was employed in Example 3 below.

EXAMPLE 3

The final polyol adsorbent residue of Example 2 was treated in a manner similar to that of Example 2. Another portion of the crude glycerine based polyol was then treated with the washed adsorbent in a manner similar to that of Example 2. The resulting polyol had an alkalinity of 3 ppm expressed as K.

EXAMPLE 4

A 70 gram portion of a filter cake consisting of 60 percent magnesium silicate adsorbent and 40 percent polyol was washed with three 45 gram portions of methanol and filtered each time. The washed adsorbent was then air dried at room temperature for 16 hours. A 400 gram portion of the crude polyol of Example 1 was stirred with 16 grams of the dried adsorbent at 95° C for 1 hour. The mixture was filtered and the polyol was found to have an alkalinity of less than 5 ppm expressed as K.

EXAMPLE 5

The procedure of Example 4 was followed with the exception that hexane was employed instead of methanol. The resulting polyol contained less than 10 ppm alkalinity expressed as K.

EXAMPLE 6

The procedure of Example 4 was followed with the exception that the filter cake was washed with three portions of hexane followed by three portions of methanol. The resulting polyol contained less than 4 ppm alkalinity expressed as K.

The embodiments of the invention in which an exclusive property or privilege is claimed are defined as follows:

1. A process for recovering the synthetic magnesium silicate or aluminum silicate adsorbent from a residue resulting from the treatment of crude polyether polyol to remove alkaline catalyst therefrom, comprising the steps of
    (a) washing spent adsorbent residue by slurrying said adsorbent residue with a solvent which is miscible with said polyol and is inert with respect to said polyol, catalyst, and absorbent, wherein said solvent is selected from the group consisting of aliphatic, alicyclic and aromatic hydrocarbons, dialkyl ketones, alkanols, dialkyl ethers, cyclic ethers, hydroxyalkyl ethers and halogenated hydrocarbons, and
    (b) removing said solvent from said adsorbent, whereby said adsorbent is reactivated to a condition suitable for treatment of further crude polyether polyol.

2. The process of claim 1 wherein the adsorbent residue is washed with solvent a plurality of times.

3. The process of claim 1 wherein the polyether polyols are selected from the group of alkylene oxide adducts of ethylene glycol, propylene glycol, diethylene glycol, dipropylene glycol, trimethylene glycol, 1,2-butanediol, 1,3-butanediol, 1,4-butanediol, hexanetriol, glycerol, trimethylolpropane, trimethylolethane, hydroquinone, pentaerythritol, α-methylglycoside, sorbitol, sucrose, ethylenediamine, diethylenetriamine, toluenediamine, aniline, methylenedianiline, piperazine, triisopropanolamine, and Bisphenol A.

4. The process of claim 3 wherein the alkylene oxide is selected from the group consisting of ethylene oxide, propylene oxide and butylene oxide.

5. The process of claim 3 wherein the polyols have a molecular weight range from about 300 to about 26,000.